United States Patent [19]
> Zuffi

[11] 4,272,521
[45] Jun. 9, 1981

[54] PURIFIED IMMUNE SERUM GLOBULIN

[75] Inventor: Timothy R. Zuffi, Kensington, Calif.

[73] Assignee: Cutter Laboratories, Inc., Berkeley, Calif.

[21] Appl. No.: 57,880

[22] Filed: Jul. 16, 1979

[51] Int. Cl.³ .................. A61K 39/395; A61K 39/00
[52] U.S. Cl. .................................... 424/85; 424/101; 424/86; 424/87; 260/112 B
[58] Field of Search .................. 424/85, 101, 177; 260/112 B

[56] References Cited

U.S. PATENT DOCUMENTS

| | | | |
|---|---|---|---|
| 3,717,708 | 2/1973 | Wada et al. | 260/112 B |
| 3,869,436 | 3/1975 | Falksveden | 260/112 B |
| 4,126,605 | 11/1978 | Schneider et al. | 424/85 |
| 4,136,094 | 1/1979 | Condie | 260/112 B |
| 4,137,307 | 1/1979 | Funakoshi et al. | 260/112 B |
| 4,165,370 | 8/1979 | Coval | 424/85 |

FOREIGN PATENT DOCUMENTS 2606118  8/1976  Fed. Rep. of Germany.

*Primary Examiner*—Delbert R. Phillips
*Assistant Examiner*—Blondel Hazel
*Attorney, Agent, or Firm*—James A. Giblin

[57] ABSTRACT

Existing and potential prekallikrein activator (PKA) can be removed from an immune serum globulin (ISG) solution using an ion exchange material to remove both existing PKA and a kallikrein-activatable precursor to PKA (Factor XII) found to be present in ISG solutions.

4 Claims, 1 Drawing Figure

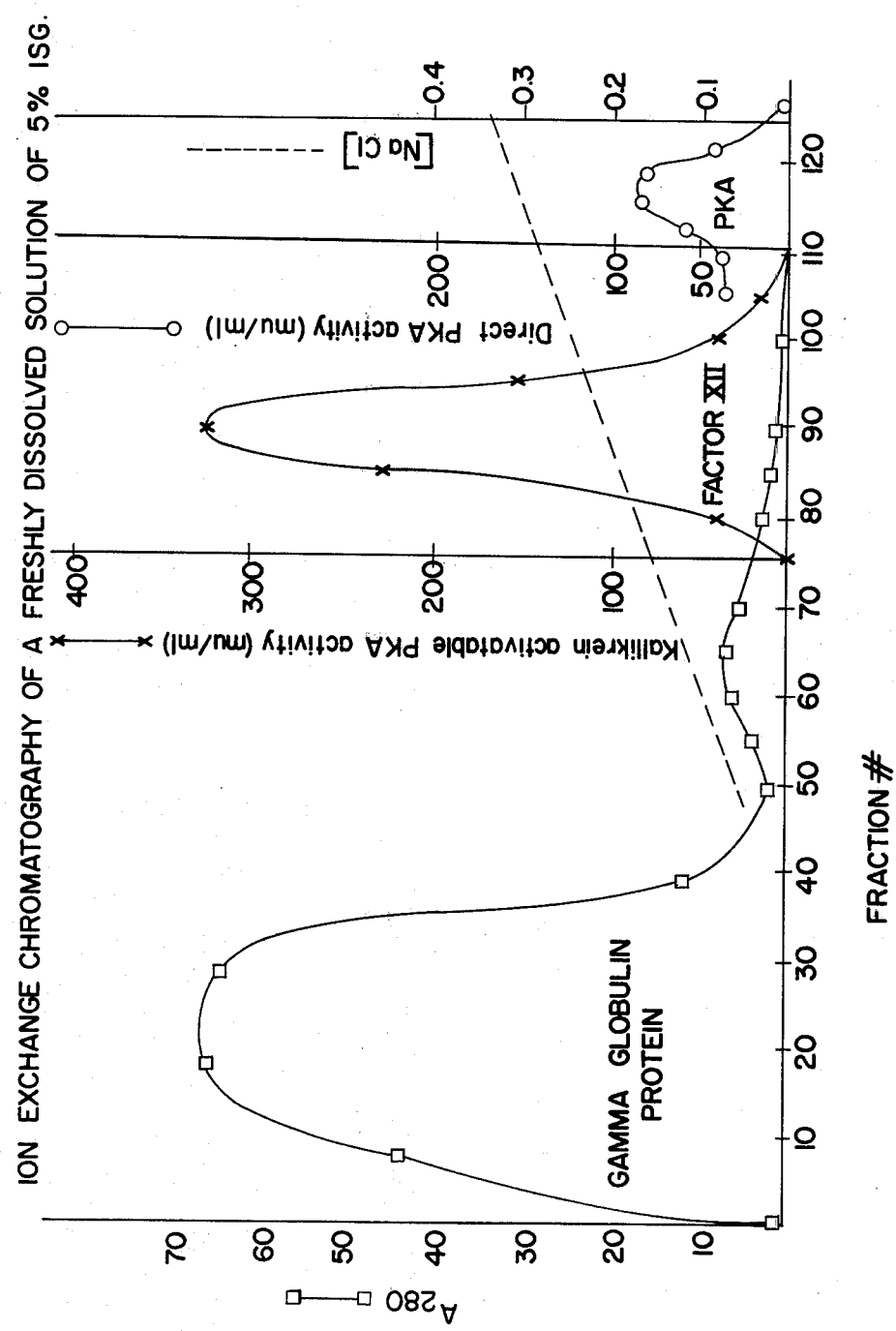

PURIFIED IMMUNE SERUM GLOBULIN

BACKGROUND OF THE INVENTION

1. Field

This disclosure relates generally to an improved immune serum globulin (ISG) preparation and specifically to an ISG preparation substantially free of existing prekallikrein activator (PKA) and PKA generated in time from a specific PKA precursor.

2. Prior Art

It is well known that the administration of ISG to patients with agammaglobulinemia has great clinical value in treating the complications of infectious disease. Unfortunately, the present route of intramuscular injection often severely limits the effective circulating levels of antibody which can be attained. In addition, direct intravenous injection of large doses of ISG is often not possible due to undesirable vasomotor responses which occasionally occur. The origin of this response is commonly attributed to the presence of IgG aggregates which bind complement and trigger an anaphylactoid reaction. The possible role of kinin system components has not been considered previously, although the presence of PKA in ISG has been pointed out.

To date, there has been no indication that any specific PKA precursors contributed to PKA activity in commercially available ISG solutions. Quite surprisingly is has now been found that both existing and potential PKA activity can be removed from ISG solutions by using ion exchange contact to remove both existing PKA activity and a kallikrein-activatable precursor to PKA previously not known to be present in such ISG solutions. Details of the ISG purification method and the product formed thereby are described below.

SUMMARY OF THE INVENTION

The purified ISG preparation comprises an aqueous ISG solution substantially free of both PKA and a kallikrein-activatable precursor to PKA, demonstrated to be Factor XII. The purification method comprises contacting an ISG solution thought to contain PKA and/or Factor XII with an anion exchange material under conditions sufficient to assure the removal of substantially all PKA and Factor XII from the ISG solution. In preferred embodiments, the purification method comprises contacting the ISG solution with an anion exchange resin (such as a QAE or a DEAE-Sephadex ® packing) under conditions sufficient to result in an ISG solution including less than 1% of the initial Factor XII activity.

BRIEF DESCRIPTION OF THE FIGURE

The FIGURE illustrates the DEAE-Sephadex chromatography of a freshly dissolved solution of a 5% ISG (Fraction II, acetone dried powder dissolved in buffer, 0.05 TRIS, 0.05 NaCl, pH 8.1), showing the respective quantities of ISG, Factor XII, and PKA activity separated under indicated conditions.

SPECIFIC EMBODIMENTS

The findings of this disclosure are based on the examination of various ISG solutions for the presence of kinin components. The studies were done to understand such component relationships and the possible generation of vasoactive materials. The identification of such components was thought to be a necessary prerequisite to finding a method for their removal and the preparation of an ISG solution free of undesireable vasoactive agents.

It had been known that significant levels of PKA activity had been occasionally observed in ISG solutions. The variability of the levels observed and an apparent tendency toward increased activity after storage prompted study of the time dependence of the appearance of PKA activity in freshly dissolved ISG solutions. When incubated at 37° C., the ISG solution demonstrated a progressively increasing level of PKA acitivity. Although the rate of appearance of this activity was slow, it was found to continue over a several day period. After 7 days, at 37° C., a greater than 10-fold increase in the level of this activity was apparent.

To determine whether this gradual appearance of PKA activity was a result of a progressive activation of kinin system components over the time course of the study, the effects of adding exogenous enzymes was examined. The results of incubating ISG solutions together with either PKA or kallikrein are shown in Table I.

TABLE I

| | PKA Generated (mu/ml) | | | |
| --- | --- | --- | --- | --- |
| Time at 37° | Kallikrein (0.45 u/ml) Treated | Kallikrein (0.23 u/ml) Treated | PKA (18 mu/ml) Treated | Buffer Control |
| 15 min. | 50.9 | 31.8 | 22.9 | 21.7 |
| 75 min. | 142.7 | 112.4 | 32.4 | 28.0 |
| 165 min. | 209.6 | 179.3 | 36.1 | 43.9 |
| 376 min. | 254 | 237.5 | 57.8 | 52.9 |
| 24 hr. | 246.7 | 245.2 | 109.8 | 108.7 |
| 4 days | — | — | 179.1 | 212.4 |
| 7 days | — | — | 174 | 219.9 |

PKA is without effect in bringing about further generation of PKA activity but kallikrein dramatically accelerates the rate of appearance of PKA. This rapid rate of PKA generation is dependent on the level of kallikrein added but a similar extent of activation was achieved in each case. Moreover, the final levels of PKA activity attained after incubation with kallikrein were comparable to that obtained when ISG is incubated alone for a much longer period. These data suggested that a pool of pre-PKA material exists in ISG solutions. The ability of kallikrein to activate this precursor to PKA suggested that potential identity of this component as Factor XII, also known as Hageman Factor, and this was tentatively confirmed by measuring Factor XII and PKA levels before and after exposure to the kallikrein treatment. See Table II.

TABLE II

| Before Kallikrein Treatment | | After Kallikrein Treatment |
| --- | --- | --- |
| XII Level | 0.7 u/ml | 0.0 u/ml |
| PKA Level | 0.136 u/ml | 3.6 u/ml |

XII levels (by coagulation assay) and PKA levels of the pooled "pre-PKA" containing fractions from DEAE-Sephadex chromatography of Fraction II powder.

The specific materials and assay methods used in the purification process and confirmation of Factor XII presence are described below.

MATERIALS AND METHODS

MES, Trizma ® base (used for preparing TRIS HCl), Benzoyl Arginine Ethyl Ester from Sigma Chemical Co., St. Louis, Missouri.

para-aminobenzamidine, ε-amino caproic acid, dithiothreitol, and iodoacetamide from Aldrich Chem. Co., Milwaukee, Wisconsin.

DEAE-Sephadex, Concanavalin A-Sepharose, Sepharose CL-4B from Pharmacia Inc., Piscataway, New Jersey.

Factor XII deficient plasma from George King Laboratories, Overland Park, Kansas.

Thrombofax Reagent (bovine brain cephalin) from Ortho Diagnostics, Inc., Raritan, New Jersey.

Prekallikrein (PK) substrate was prepared by diafiltering freshly drawn citrated human plasma at room temperature extensively against 0.05 M Tris HCl, pH 8.0 and then passing it through a column of DEAE-Sephadex equilibrated in the same buffer. The unbound fractions containing the majority of the PK activity, were pooled and absorbed batchwise with Concanavalin A-Sepharose for 2 hours at room temperature. The Con A-Sepharose was then collected on a Buchner funnel, washed with Tris buffer; the bound PK was then eluted with the same buffer containing 0.2 M α-methyl-D-glucoside. The PK substrate obtained from this procedure was essentially free of activation, as no spontaneous generation of kallikrein occurred after 24 hours at room temperature.

Prekallikrein Activator (PKA)

PKA was prepared from Cohn Fraction III obtained from Cutter Laboratories, Inc., Berkeley, California. The fresh Fraction III paste was dissolved in an 0.05 M Tris HCl buffer, pH 8.0, and the solution was absorbed batchwise with DEAE-Sephadex, equilibrated in the same buffer. The DEAE-Sephadex was removed on a sintered glass funnel and washed with more starting buffer and finally with starting buffer containing 0.5 M NaCl. The 0.5 M NaCl washes—containing the PKA—were concentrated by ultrafiltration and exchanged with PBS buffer (0.05 M NaH$_2$PO$_4$, 0.15 M NaCl, pH 7.5) by diafiltration.

Benzamidine-EACA-Sepharose

Sepharose CL-4B (Pharmacia) was activated with cyanogen bromide at pH 11.0 at room temperature, and ε-amino caproic acid was coupled to the activated resin at pH 9.5 overnight. After washing well, the pH was adjusted to 5.6, and the material was treated with carbodiimide briefly before the addition of para-aminobenzamidine.

Kallikrein

This enzyme was prepared by mixing the purified prekallikrein preparation with a catalytic amount of the concentrated PKA at room temperature and allowing the conversion to kallikrein to go to completion. This mixture was then applied to the benzamidine-EACA-Sepharose column equilibrated in 0.05 Tris HCl, pH 8.0. After a brief buffer wash, a linear arginine gradient was applied. The kallikrein-containing fractions were pooled, the pH adjusted to 6.0 (exchanged with 0.1 M MES buffer pH 6.0), and concentrated by ultrafiltration to 4.5 BAEE u/ml. The yield after ultrafiltration was 93% and the specific activity was 16.8 BAEE units per A$_{280}$. This material is reported to be extremely pure. SDS-PAGE of the preparation revealed a single band of M.W. 85,000.

Assay for PKA

The assay for PKA was a coupled assay in which the kallikrein produced from prekallikrein by a limited amount of PKA is determined by initial rate assay with BAEE. Prekallikrein substrate (50λ) and sample to be tested for PKA (25λ) are incubated together at 37°. At 5 minutes, a 25λ aliquot is removed and mixed with 2 ml of 0.05 mM BAEE in PBS buffer, pH 8.0 at 37° and the hydrolysis rate recorded continuously at 253 mM in a spectrophotometer with a thermostatted cuvette holder at 37°.

In the assay, the concentration of prekallikrein substrate was determined to be sufficiently above the K$_m$ for the enzyme PKA such that the rate of conversion of prekallikrein to kallikrein is pseudo first order in prekallikrein. Thus, the equation for calculating levels of PKA:

$$PKA\ (u/ml) = 3/t \ln \frac{PK_o}{PK_o - K_t}$$

assumes a reaction rate which is proportional to the PK concentration as well as to the constant PKA concentration.

In this equation, "3" is the dilution factor for sample in the incubation mixture; t is time of incubation which we have kept constant at 5 minutes; K$_t$ is the amount of kallikrein formed at the specified incubation time i.e. the ΔA$_{253}$/min; and PK$_o$ is the starting level of prekallikrein.

The assay is sensitive to PKA levels of 2 mu/ml and is most accurate below 60% conversion of PK to K.

Assay for Pre-PKA Activity (Factor XII)

The assay for the precursor of active PKA involves an incubation at 37° of 0.9 ml sample and 0.1 ml of kallikrein of concentration 4.5 BAEE u/ml for sufficient time to allow complete conversion to the active enzyme. The results indicated that about 400 minutes is the minimum allowable time. After this incubation, 25λ aliquots were removed and assayed for PKA in the usual way. Since there is detectable kallikrein activity carried over into the samples, the measured ΔA$_{253}$ must be corrected for by subtracting this background before calculating PKA content.

Factor XII Coagulation Tests

Factor XII was tested for its ability to correct the clotting time of congenitally-dificient plasma in a Fibrometer ® using a normal pooled plasma as a control.

EXAMPLE

Separation of Pre-PKA from the Immunoglobulin Fraction of ISG

A 5% ISG solution (200 ml) was chromatographed on DEAE-Sephadex at pH 8.1 in a buffer consisting of 0.05 M Tris-HCl and 0.05 M NaCl. Fractions of 7.5 ml were collected. Under these conditions, the major protein peak of immunoglobulin is not retained by the column, as shown in the FIGURE. However, a peak of kallikrein-activatable pre-PKA was bound by the column and eluted in a salt gradient at a total concentration of 0.22 M NaCl. These elution characteristics were found to be similar to those shown previously for Factor XII.

In addition, a peak of PKA activity also eluted during the salt gradient. This activity was found at a salt concentration of 0.32–0.34 M and was well separated from the peak of pre-PKA material. The binding of both PKA and the pre-PKA fraction to DEAE resulted in a virtually complete removal of these activities from ISG. This is shown in the FIGURE and Table III below for a freshly dissolved preparation of ISG. No change in the purity of electrophoretic migration of ISG due to DEAE-Sephadex chromatography was observed by immunoelectrophoresis versus anti-whole human serum.

TABLE III

| Relative Factor XII and PKA Amounts in 5% ISG | | |
|---|---|---|
| | Factor XII | PKA |
| Before ion exchange Chromatography | 250 mu/ml | 22 mu/ml |
| After ion exchange | <2 mu/ml | <2 mu/ml |

The Factor XII or "pre-PKA" was determined by treatment with kallikrein for sufficient time to complete activation to PKA.

Characterization of Pre-PKA

The pre-PKA fraction, partially purified by the DEAE-Sephadex chromatography, was tested for Factor XII activity by a coagulation assay employing the Factor XII devicient plasma. From the FIGURE, it is evident that the isolated pre-PKA fraction demonstrates considerable Factor XII activity while at the same time showing little PKA activity. The identity of the pre-PKA as Factor XII was confirmed by immunoelectrophoresis versus a specific antiserum to human Factor XII.

After incubation of the Factor XII with kallikrein for a sufficiently long period to insure complete activation to PKA, essentially no coagulation activity was observed. The level of PKA activity attained is thus due to a direct conversion of Factor XII to PKA by kallikrein, consistent with the activation sequence for the kinin system.

As shown above, the observation that both PKA and Factor XII bind to DEAE-Sephadex at pH 8.0 permitted the separation of both of these activities from the major IgG fraction of ISG. This results in a preparation of ISG which is essentially free of PKA activity and, perhaps more importantly, is free of the potential for subsequent generation of PKA from Factor XII. It should be understood that other known anion exchange resins may be used (e.g. QAE-Sephadex gave similar results).

It is thought that the purified ISG preparation of this disclosure may be useful for intravenous administration, thus avoiding the necessity of chemically modifying ISG for intravenous use.

I claim:

1. A method of removing Factor XII from an immune serum globulin preparation which comprises contacting the preparation with an ion exchange material at a pH of $\geq 7.2$ under conditions sufficient to assure removal of substantially all of the Factor XII.

2. The method of claim 1 wherein the immune serum globulin preparation is subjected to anion exchange chromatography.

3. The method of claim 1 wherein the removal method utilizes a total ionic concentration less than that concentration which results in elution of the Factor XII from the anion exchange resin.

4. The method of claim 3 wherein the ionic species comprises NaCl at a concentration of less than about 0.2 M, at a pH of about 8.1.